US012702556B2

(12) United States Patent
Genovese et al.

(10) Patent No.: US 12,702,556 B2
(45) Date of Patent: Aug. 11, 2026

(54) ANNULUS REPAIR METHODS AND SYSTEMS

(71) Applicant: MEDTRONIC, INC., Minneapolis, MN (US)

(72) Inventors: Matthew E. Genovese, Windsor, CA (US); Karan P. Punga, San Rafael, CA (US); Olivia P. Metcalf, Cambridge, MA (US); William W. Chang, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 445 days.

(21) Appl. No.: 18/563,886

(22) PCT Filed: May 24, 2022

(86) PCT No.: PCT/IB2022/054853
§ 371 (c)(1),
(2) Date: Nov. 23, 2023

(87) PCT Pub. No.: WO2022/249062
PCT Pub. Date: Dec. 1, 2022

(65) Prior Publication Data

US 2024/0225838 A1 Jul. 11, 2024

Related U.S. Application Data

(60) Provisional application No. 63/192,917, filed on May 25, 2021.

(51) Int. Cl.
*A61F 2/24* (2006.01)

(52) U.S. Cl.
CPC .......... *A61F 2/2466* (2013.01); *A61F 2/2445* (2013.01); *A61F 2/2496* (2013.01); *A61F 2220/0016* (2013.01); *A61F 2250/001* (2013.01)

(58) Field of Classification Search
None
See application file for complete search history.

(56) References Cited

U.S. PATENT DOCUMENTS

2008/0306586 A1* 12/2008 Cartledge ............. A61F 5/0003 623/2.11
2010/0121433 A1* 5/2010 Bolling ............ A61B 17/00234 623/2.11

(Continued)

OTHER PUBLICATIONS

International Search Report and Written Opinion, PCT/IB2022/054853, mailed Sep. 1, 2022.

*Primary Examiner* — Shaun L David
(74) *Attorney, Agent, or Firm* — Medler Ferro Woodhouse & Mills PLLC

(57) ABSTRACT

Aspects include systems having an implant (e.g., annuloplasty implant) and a delivery device. The delivery device includes a delivery catheter and a sizing device. The sizing device has a frame including a plurality of struts and a plurality of anchor housings interconnected to at least one respective strut. An anchor is positioned within each of the anchor housings in a delivery arrangement. In the delivery arrangement, the sizing device and the implant are positioned within the catheter and each anchor is within one of the plurality of anchor housings. The delivery device further having an adjustment arrangement in which the implant, anchors and at least a portion of the sizing device are positioned outside of the catheter. The delivery device further having a deployed arrangement in which the frame is disconnected from the anchors and the frame is withdrawn into the delivery catheter. Related methods are also disclosed.

20 Claims, 7 Drawing Sheets

(56) References Cited

U.S. PATENT DOCUMENTS

| | | | | |
|---|---|---|---|---|
| 2016/0120645 | A1* | 5/2016 | Alon | A61F 2/2442 623/2.4 |
| 2017/0135816 | A1 | 5/2017 | Lashinski | |
| 2018/0228610 | A1* | 8/2018 | Lashinski | A61F 2/2466 |
| 2019/0029827 | A1 | 1/2019 | Bar et al. | |
| 2020/0289265 | A1 | 9/2020 | Gifford, III et al. | |
| 2021/0220133 | A1* | 7/2021 | Anderson | A61F 2/2418 |

* cited by examiner

ANNULUS REPAIR METHODS AND SYSTEMS

FIELD

The present technology is generally related to annulus repair methods and systems provided to reduce the diameter or dimensions of an implant that is anchored to an annulus. In one non-limiting example, the annulus is a heart valve annulus.

BACKGROUND

Generally, the anatomy and physiology of the human heart is well known. Of the four one-way valves in the heart, the two inlet valves are the mitral valve of the left side of the heart, and the tricuspid valve on the right side of the heart. The tricuspid valve is located between the right atrium and the right ventricle. The three leaflets of the tricuspid valve laterally terminate at the tricuspid annulus. Blood flows from the superior and inferior vena cava into the right atrium, then through the tricuspid valve during diastole to fill the right ventricle. During ventricular systole, the tricuspid valve is closed and blood is ejected through the pulmonary valve into the pulmonary artery and hence through the lungs. At the end of ventricular systole the pulmonary valve closes. Leaving the lungs, the now oxygenated blood flows into the left atrium and hence through the mitral valve into the left ventricle during ventricular diastole. Finally, at ventricular systole the mitral valve closes and blood is ejected through the aortic valve into the aorta. However, should the mitral valve become regurgitant due to disease then some percentage of the left ventricular stroke volume will flow backwards through the mitral valve into the left atrium. This regurgitation causes the left atrial pressure to rise, in turn causing pulmonary artery pressure to rise, which is reflected back to the right ventricular pressure.

Typically, to treat a patient with functional mitral regurgitation, a physician places an annuloplasty ring on the mitral annulus to reduce the circumference and septal-lateral diameter of the annulus. In degenerative mitral regurgitation patients, annuloplasty rings are utilize to stabilize the mitral annulus, not reduce the annular circumference.

The present disclosure addresses problems and limitations associated with the related art.

SUMMARY

The techniques of this disclosure generally relate to systems and methods of delivering an implant to an annulus that can be anchored and reduced in diameter or other dimension to reduce a size of the annulus. In one non-limiting example, the devices and methods of the disclosure can be used to treat mitral regurgitation. Various examples of the disclosure provide for versatility and control in how the implant is reduced in diameter or dimension to allow patient-specific treatment. In addition, various examples of the disclosure enable future procedures or adjustments to the implant.

In one aspect, the present disclosure provides a system having an implant and a delivery device. The delivery device includes a delivery catheter and a sizing device at least partially housed within the delivery catheter. The sizing device has a frame including a plurality of struts and a plurality of anchor housings interconnected to at least one respective strut. One of a plurality of anchors is positioned within each of the anchor housings in a delivery arrangement. In the delivery arrangement, the sizing device and the implant are positioned entirely within the delivery catheter and each anchor is within one of the plurality of anchor housings. The delivery device further has an adjustment arrangement in which the implant, anchors and at least a portion of the sizing device are positioned outside of the delivery catheter. The delivery device also has a deployed arrangement in which the frame is disconnected from the plurality of anchors and the frame is withdrawn into the delivery catheter.

In another aspect, the disclosure provides a method including the steps of providing a system including an implant and a delivery device in a delivery arrangement. The delivery device includes a delivery catheter having a distal end, and a sizing device at least partially housed within the delivery catheter. The sizing device has a frame including a plurality of struts and a plurality of anchor housings interconnected to at least one respective strut; wherein one of a plurality of anchors is positioned within each of the anchor housings in a delivery arrangement. The method further includes directing the distal end to an annulus of a patient and distally advancing the plurality of anchor housings out of the distal end. The method includes positioning the plurality of anchor housings around the annulus and advancing the plurality of anchors into the annulus. Then, the plurality of anchors are detached from the frame. The method additionally includes withdrawing the frame into the delivery catheter and withdrawing the frame and the delivery catheter from the patient.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

Specific embodiments of the present disclosure are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician.

Generally, a bodily annulus, such as a mitral valve annulus, does not have a mathematically round or circular shape or opening. As such, a "diameter" of the annulus is often irregular. When the present disclosure references reducing a "diameter" of the valve annulus or any other bodily annulus for that matter, it is intended that at least one dimension between two points of the annulus is shortened to reduce the size or perimeter of the annulus (e.g., as is generally recognized as a method for treating valve regurgitation).

Figure 1:
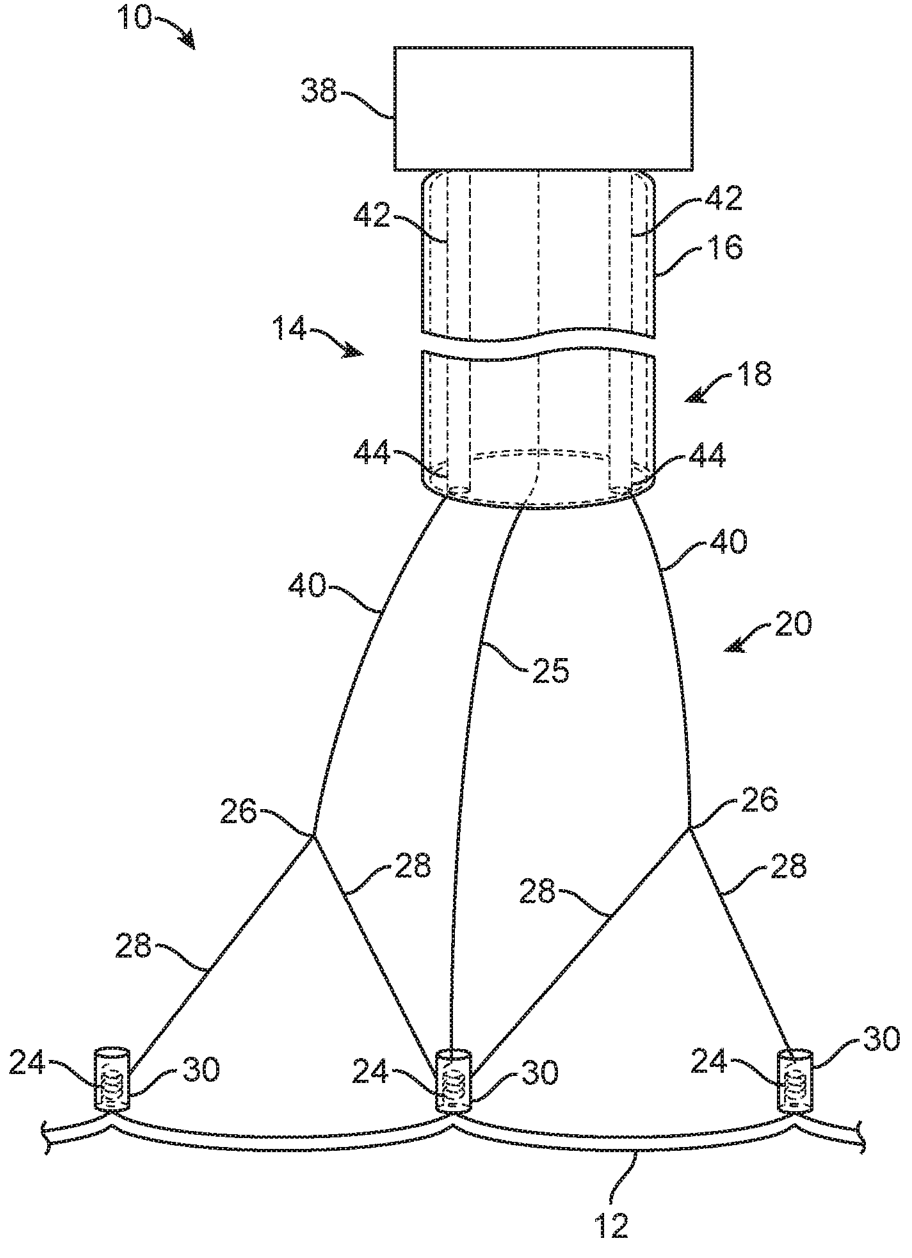
FIG. 1 is a schematic diagram of a system of the disclosure having a sizing assembly supporting an implant.
Figure 2:
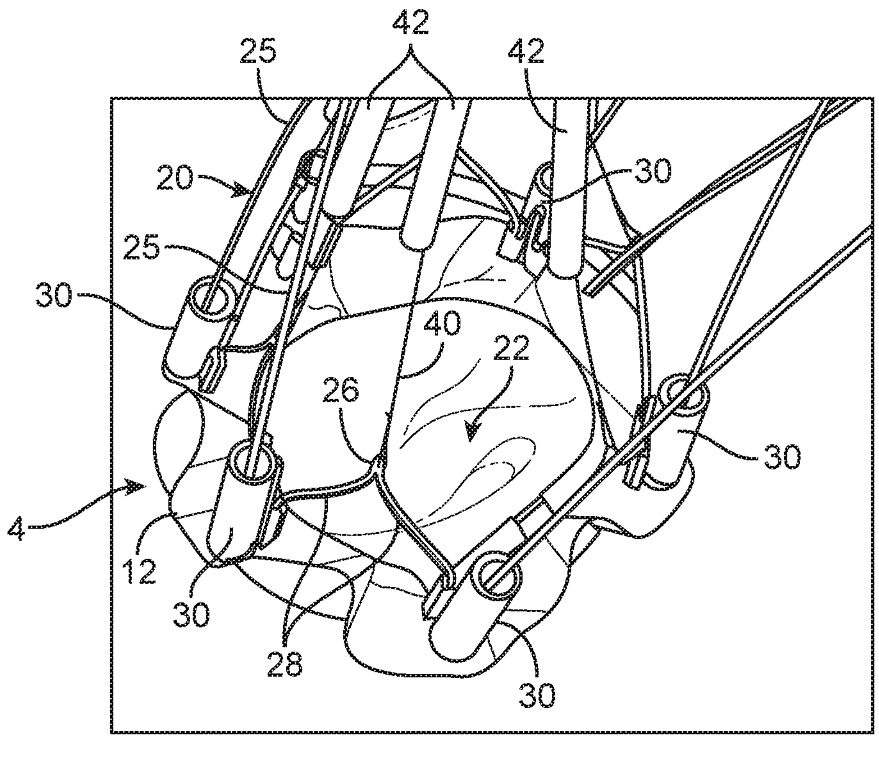
FIG. 2 illustrates the system of FIG. 1 showing the sizing assembly supporting the implant for deployment around a valve annulus.
Figures 3A, 3B:
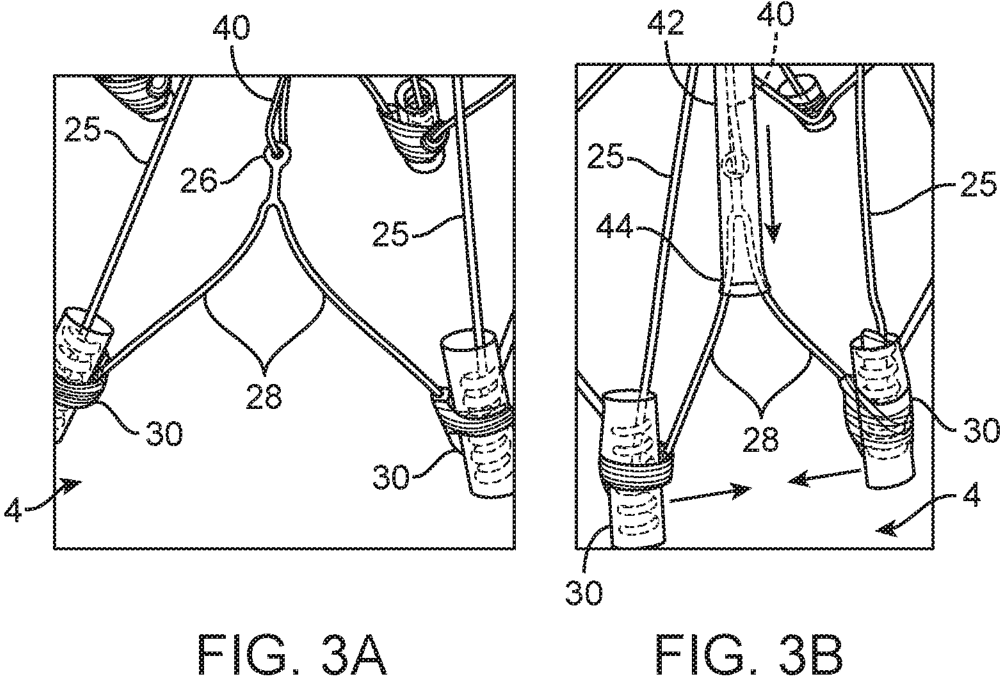
FIG. 3A is an enlarged view of the system of FIG. 2 in a pre-cinched arrangement prior to resizing the valve annulus.
FIG. 3B illustrates the system shown in FIG. 3B in a cinched arrangement after resizing the valve annulus.
Figure 4:
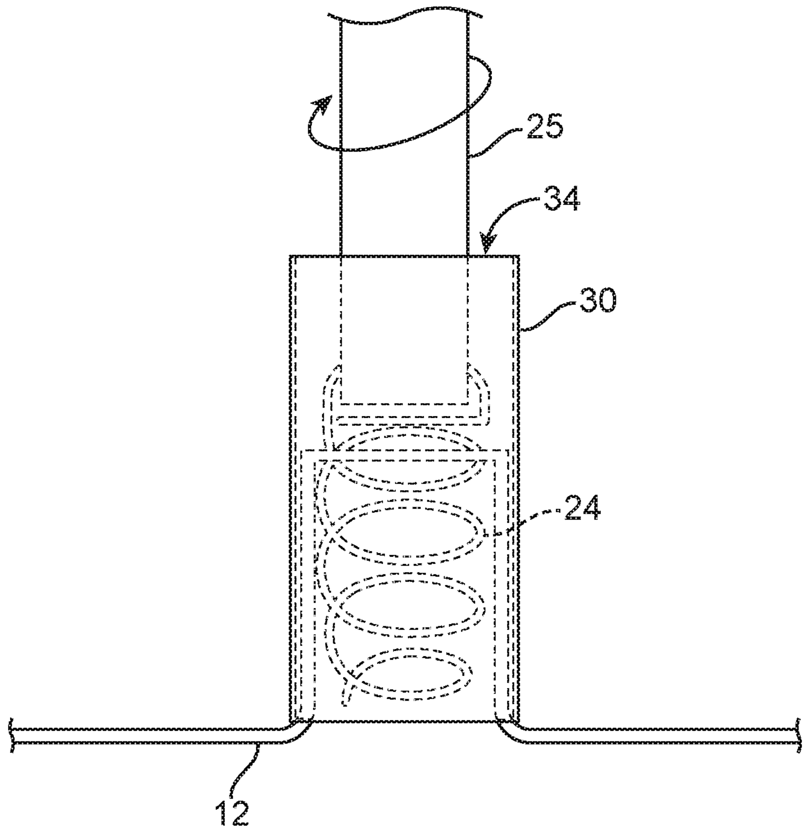
FIG. 4 is a schematic illustration of an implant, anchor housing, anchor and drive shaft of the system of FIGS. 1-3B.

One system 10 of the disclosure is collectively illustrated in FIGS. 1-10B. Generally, the system 10 includes an annuloplasty implant 12 and a delivery device 14 including a delivery catheter 16 and a sizing device 18 having a frame 20. The frame 20 functions as a platform to control the size and dimensions of an interior opening 22 (FIG. 2) formed by an implant 12 and provide stability for steering the implant 12 to a treatment location for anchoring with at least one anchor 24. Systems and methods of the disclosure can be used with a variety of implants. Such implants can include annuloplasty bands or rings, either defining a closed opening or partially-closed opening, that are made at least in part of implantable fabric, implantable tissue, or other implantable elastic material. Non-limiting examples include implants made at least in part of pericardial bovine tissue, polyester, or poly-paraphenylene terephthalamide. The implants may further include shape supporting wires and spines, as desired. In addition, the implants may be configured to receive and maintain one or more elongated lock wires or members, as will be discussed in greater detail below with respect to FIGS. 10A-10B. Actuation of one or more elements of the system 10 can optionally be accomplished with a handle assembly 38 optionally provided as part of the system 10. In FIG. 1, the delivery catheter 16 and handle assembly 38 are shown schematically and are not to scale or reflective of proportion.

The frame 20 optionally includes a plurality of crowns 26 interconnecting a plurality of struts 28 (generally referenced). In one example, which is perhaps best shown in FIG. 3A, each crown 26 is configured to join two adjacent struts 28. Alternatively, each crown 26 may generally designate a juncture between two adjacent struts 28. Attached to each strut 28, opposite the respective crown 26, is an anchor housing 30 that houses one pre-loaded anchor 24. It is noted that oftentimes only a select few of the struts 28, anchors 24, and anchor housings 30, for example, are referenced in the figures for ease of illustration. The disclosure is further not intended to be limited to a particular number of anchors/anchor housings. In one example, the device 14 includes six anchor housings 30 to accommodate six anchors 24. In another example, the device 14 includes eight anchor housings 30 to accommodate eight corresponding anchors 24. In various examples, as perhaps best shown in FIG. 4, one or more anchor housings 30 includes a cylindrical body 32 made of plastic or metal defining an opening 34 having internal threads (not visible) that correspond to a helix formed by the anchor 24. In some examples, the anchor 24 is entirely positioned within the anchor housing 30 to provide for an atraumatic assembly prior to deployment. In such examples, the implant 12 can be partially positioned within the anchor housing 30. The present disclosure is not intended to be limited to any particular anchor or anchor housing configuration. Each anchor 24 can be of the type including, but not limited to helical (single or double) or push/pronged style anchors as known in the art. In one example, the implant 12 is releasably secured to the frame 20 for delivery at each anchor housing 30 with the respective anchor 24 until the anchor 24 is deployed from the respective anchor housing 30. In various examples, the implant 12 is releasably attached to the frame 20 with one or more sutures 31 (see also, FIG. 6) that can be severed once release of the frame 20 from the implant 12 is desired.

Figure 5:
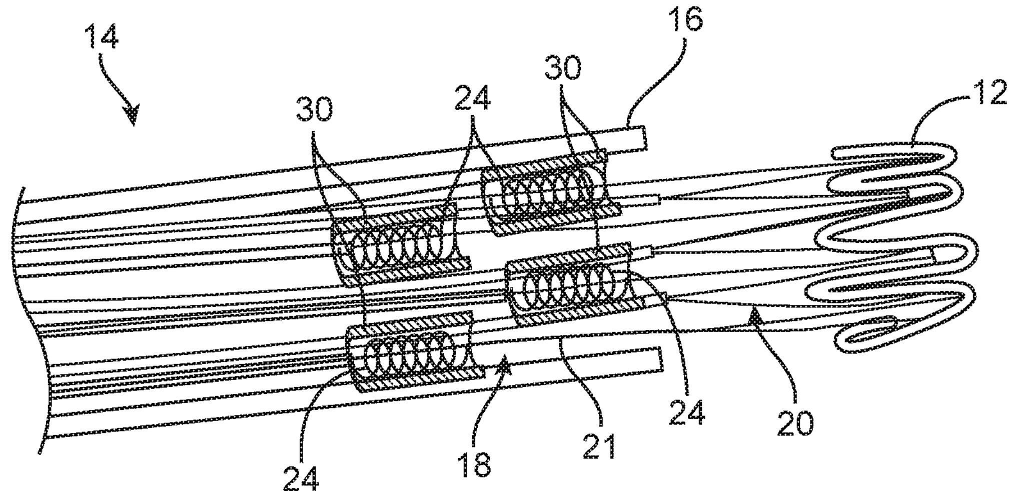
FIG. 5 is a schematic illustration of select components of the system of FIGS. 1-4 in which the sizing assembly is at least partially positioned within a guide catheter for delivery to the valve annulus.
Figure 6:
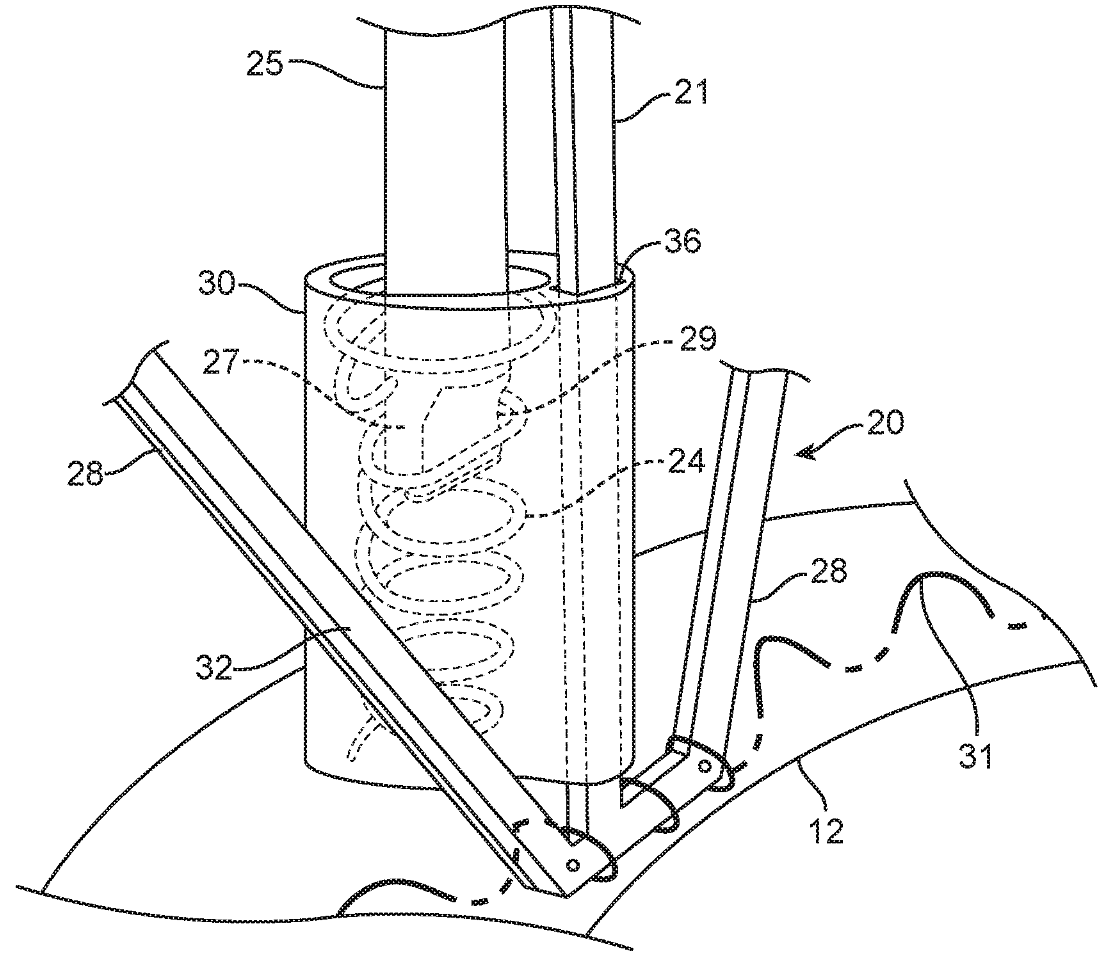
FIG. 6 is a schematic illustration of the anchor housing of FIG. 4 and frame of FIG. 1 having modifications to enable the delivery arrangement of FIG. 5.

One example of a partially-loaded configuration of the sizing device 18 within the delivery catheter 16 is generally shown in FIG. 5. In this example, the anchors 24 (within anchor housings 30) are staggered along a length of the delivery catheter 16 to reduce the delivery catheter 16 profile when the frame 20 is in the collapsed, delivery configuration within the delivery catheter 16. It is to be understood that in the collapsed, delivery configuration, the entire sizing device 18 and implant 12 would be positioned within the delivery catheter 16. The delivery catheter 16 can be sized to have a smaller profile when the anchors 24 and anchor housings 30 are staggered. In one example, the anchors 24 are supported in their staggered arrangement, from their final position around the annulus 4, on either a guide wire or an extension 21 of the frame 20 which extends into a distal end of the delivery catheter 16. In the example of FIG. 6, the anchor housing 30 is configured to be slidable with respect to the frame 20. The anchor housing 30 can include a frame lumen 36, separate from the opening 34, configured to receive the optional extension 21 of the frame 20. Movement of the anchor housings 30 along the extension 21 can be controlled with respective manipulation members 40. In various embodiments, the anchor housings 30 and extensions 21 are configured so that the anchor housing 30 cannot rotate with respect to the extension 21. In the example shown, the frame lumen 36 defines a rectangular opening to receive the rectangular shaped extension 21. Staggering of the anchors 24 and anchor housings 30 can also made possible because any desired delivery of an intra-cardiac echo catheter 54 or the like can be conducted after the frame 20 has transitioned to the expanded arrangement, which frees up space within the delivery catheter 16. After the frame 20 has transitioned to the expanded arrangement and has been roughly placed in position on the annulus 4 (see FIG. 6), one or more anchor housings 30 (including pre-loaded anchors 24) can be distally advanced and pushed distally into place at the distal end of the frame 20 along the extension 21.

Figure 7:
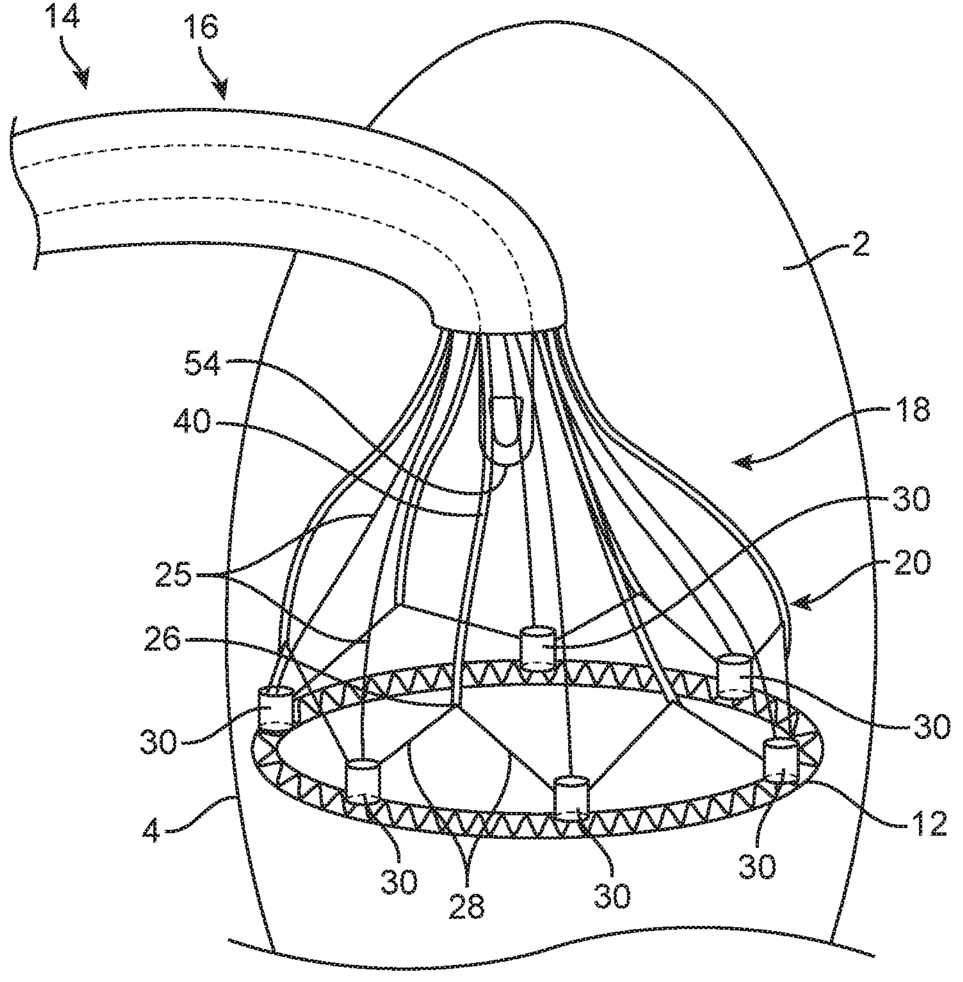
FIG. 7 is a schematic illustration of the system of FIG. 1 delivered to a valve annulus such that the implant resides at the valve annulus.
Figure 8:
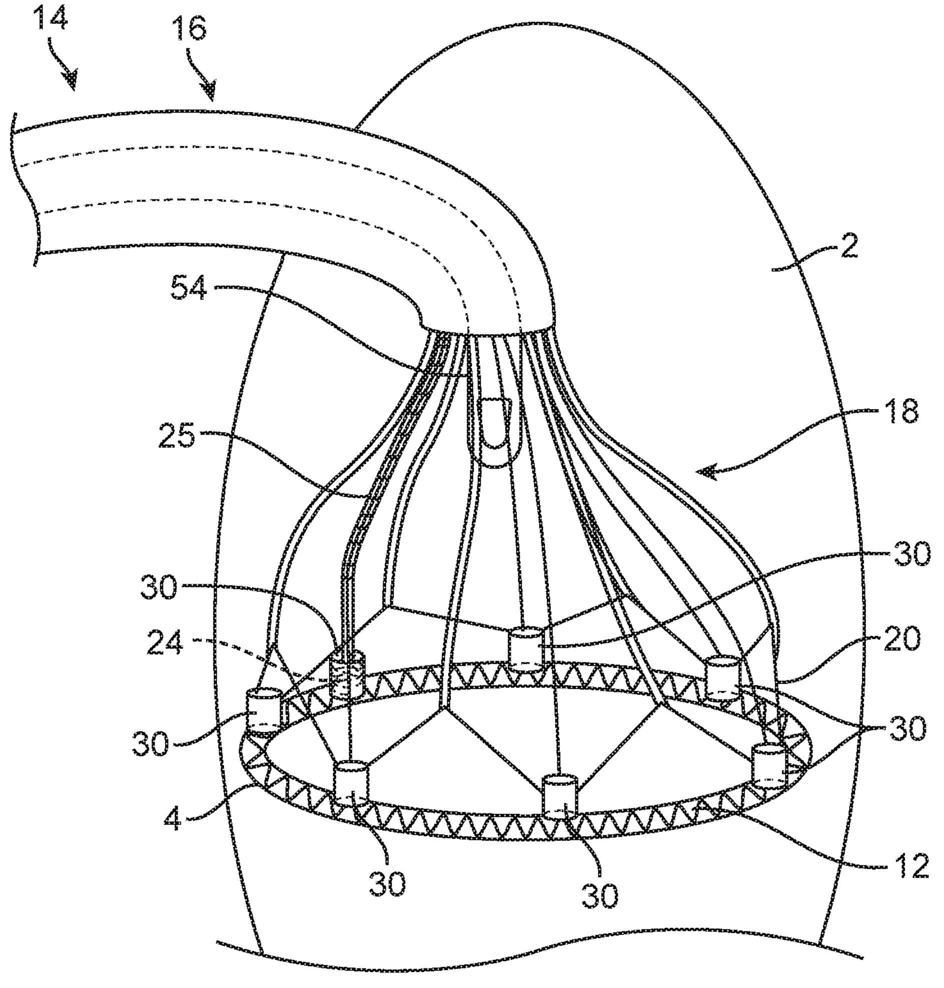
FIG. 8 is a schematic illustration of the system of FIG. 7 having at least one drive shaft engaged with one anchor to drive the anchor into the valve annulus.
Figure 9A:
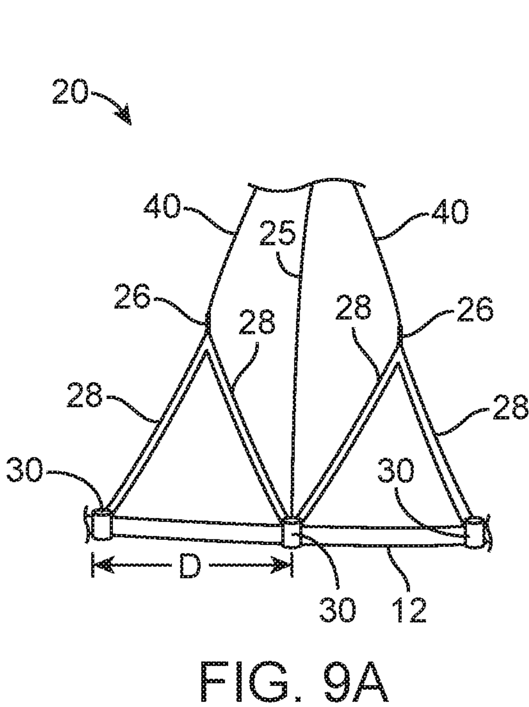
FIG. 9A is a partial, schematic illustration of the system of FIG. 1 in the pre-cinched arrangement.
Figure 9B:
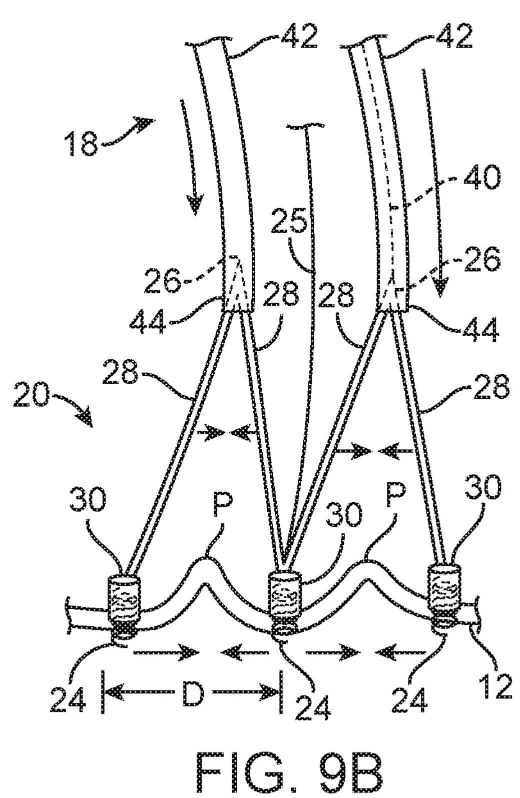
FIG. 9B is a partial, schematic illustration of the system of FIG. 9A in the cinched arrangement in which annular tissue secured to the implant is plicated between two adjacent anchors due to a reduction in the distance between the two adjacent anchors.

In various embodiments of the disclosure, each anchor 24 is deployed from the respective anchor housing 30 via a shaft 25. As best shown in FIG. 6, the shaft 25 can optionally include a D-shaped tip 27 that is shaped to correspond to an opening 29 in the anchor 24. In one embodiment, the delivery device 14 includes one shaft 25 for each anchor 24 as is generally shown in FIG. 7 although not every shaft 25 is referenced for ease of illustration. Various shafts 25 of the disclosure may be configured for mere proximal and distal movement with respect to the delivery catheter 16 and other shafts 25 may be configured for torqueing or rotational movement with respect to the delivery catheter 16. It is envisioned that any corresponding anchor and shaft constructions that allow for the shaft to advance and release the respective anchor within the annulus are suitable and within the scope of the present disclosure.

Attached to each crown 26 is a manipulation member 40. The manipulation member 40 can be a wire, shaft or similar structure for control of the frame 20. Only select manipulation members 40 are referenced for ease of illustration. It is envisioned that one manipulation member 40 is provided to interconnect each pair of struts 28. In various embodiments, the crown 26 includes an aperture in which the manipulation member 40 can be tied, or vice versa. In some embodiments, the manipulation member 40 is rigid to provide the ability to push or distally advance the frame 20. If the manipulation member 40 is rigid, the manipulation member can be used for steering and placement, assisting to push and pull the anchors 24 into desired positioning. If only a pulling function of the frame 20 is required, the manipulation member 40 may be non-rigid, such as a suture, filament or cord. Each manipulation member 40 can be connected to the handle assembly 38 (schematically shown), which can optionally be utilized to actuate the manipulation member 40 to move the frame 20 within an atrium 2 to assist in locating the annulus 4. The system 10 can further include one or more tubes 42 that can be delivered through the delivery catheter 16 via optional actuation by the handle assembly 38. Each tube 42 can be positioned and tracked over one manipulation member 40 to cinch (i.e. reduce a perimeter or inner area dimension(s) of) the implant 12 and the annulus 4 secured thereto by moving adjacent frame struts 28 together, which correspondingly draws adjacent anchor housings 30 and anchors 24 closer together. In various embodiments, the tubes 42 are braided polymer catheters or are otherwise made of a spring biased material to compress the respective crown 26 and struts 28 as the tube 42 is distally advanced over the respective crown 26 and struts 28 as is perhaps best shown in FIGS. 3A and 3B. Alternatively, one or more components of the frame 20 (e.g., manipulation members 40, crowns 26 and/or struts 28) and a distal end 44 of the respective tube 42 could be correspondingly threaded so instead of pushing and pulling the tube 42 proximally or distally with respect to the frame 20, the tube 42 is torqued onto the respective crown 26 to draw adjacent struts 28, anchor housings 30 and anchors 24 closer together. It is believed that a threaded connection may provide superior stability and connection during implant placement and adjustment. In other words, a maximum distance between adjacent struts 28 can be reduced to draw respective anchor housings 30 closer together. Movement of the tubes 42 can optionally be achieved with the handle assembly 38, for example.

In order to reduce the diameter of the frame 20 and thus, achieve a cinching or reduction in a diameter or dimension of the implant 12 and annulus 4 secured thereto, many methods can be employed. In one illustrative and non-limiting method, the system 10 is delivered in the delivery arrangement through the atrium 2 to the annulus 4 to be treated. As shown in FIG. 7, the frame 20 is distally advanced out of the delivery catheter 16 so that the frame 20 expands to its natural arrangement and the implant is loosely positioned around the annulus 4. The intra-cardiac echo catheter 54 can optionally be utilized to confirm the implant 12 positioning. Once the implant 12 is in position, the shafts 25 can be used to at least partially deploy the anchors 24 from the anchor housings 30 into the annulus 4 to at least partially secure the implant 12 to the annulus 4. Then, the tubes 42 positioned over the manipulation members 40 can be pushed over the crowns 26 of the frame 20, forcing the adjacent struts 28 together to cause a local plication P of the annulus tissue. The tubes 42 allow for segments of annulus tissue positioned between adjacent struts 28 to be plicated to different degrees around the annulus, where advancing a distal end 44 of the respective tube 42 further down (i.e. in a direction toward the implant 12) on the frame 20 causes a greater degree of plication and keeping the distal end 44 of the respective tube 42 higher (i.e. in a direction away from the implant 12) on the crown 26 causes a lesser degree of plication. It will be understood that by reducing a distance D between anchors 24/anchor housings 30, as actuated by reducing a maximum distance between adjacent struts 28, plication will be achieved. Alternatively, as indicated above, components of the frame 20 and distal ends 44 of the tubes 42 can be cooperatively threaded so that rotational movement of the tube 42 correspondingly moves the distal end 44 of the tube 42 proximally or distally with respect to both the crowns 26, struts 28 and anchor housings 30. Torqueing or advancement of the tube 42 can be accomplished with the handle assembly 38, for example.

Figure 10A:
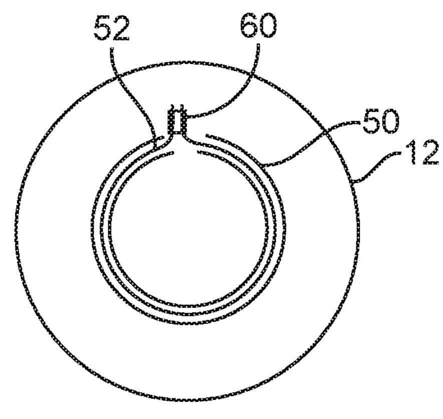
FIG. 10A is a schematic illustration of an implant of the disclosure having at least one elongated lock member maintained therein.
Figure 10A:
Figure 10B:
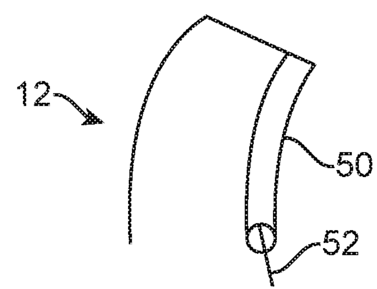
FIG. 10B is a partial, schematic illustration of the implant of FIG. 10A showing a lumen formed by the implant for at least partially housing the at least one elongated lock member.

Referring now in particular to FIGS. 10A-10B, to optionally lock the implant 12 in position on the annulus 4 after the diameter or opening of the annulus 4 has been resized to effectively maintain the implant 12 and annulus 4 reconfiguration, the implant 12 can include a lumen 50 to house a cinch maintenance wire 52. Once the desired cinched state of the annulus 4 has been achieved through manipulating the crowns 26 of the frame 20, the cinch maintenance wire 52 can be pulled taught and locked in position with lock 60. This cinch maintenance wire 52 holds the position of the anchors 24 with respect to the annulus 4. Then, the anchors 24 can be driven into the annulus 4 further (e.g., two full rotations) to fully deploy the anchors 24 within the tissue of the annulus 4 and from the anchor housings 30 so that the anchors 24 can be fully released from the frame 20. Then, the frame 20 is ready to be removed from the anchored implant 12, leaving only the anchors 24 and implant 12 behind at the annulus 4. This method including the removal of the frame 20 is particularly advantageous as it enables future procedures or adjustments to be made to the previously implanted implant 12 on the annulus 4. Additional locking mechanisms may also be employed in various embodiments and the disclosure is not intended to be limited to any particular technique. It will be further understood that other bodily annuluses can be modified using similar methods.

Example 1

The sizing device 18 is delivered in a collapsed arrangement within the delivery catheter 16 to the atrium 2 within the delivery catheter 16. Elements of the frame 20 can be made of a shape memory material (e.g., nitinol). The sizing apparatus 18 can therefore be compressed within the delivery catheter 16 in a compressed arrangement has a reduced diameter as compared to an expanded, normal arrangement. Once the delivery catheter 16 is in position at the annulus 4, the frame 20 can be distally advanced at least partially out of the delivery catheter 16 so that the frame 20 is allowed to naturally expand by simply extending the frame 20 outside of the delivery catheter 16. The manipulation members 40 can be used to find the annulus 4 and properly position the frame 20 and implant 12 around the annulus 4. In some methods, the delivery catheter 16 maintains and can deliver an intra-cardiac echo catheter 54 to assist in finding the most desired anchoring locations. The intra-cardiac echo catheter 54 can further be advanced into the approximate center of the annulus 4, within the atrium 2, and then rotated to view each anchor housing 30 (housing anchor 24) individually. When the sizing device 18 is in the desired position, the anchors 24 can be deployed in whatever sequence desired. Anchors 24 can be initially partially deployed within annulus 4 tissue such that they are partially secured within tissue while still being interconnected to the respective anchor housing 30 until all anchors 24 are partially deployed, the anchors 24 can be full deployed to release the anchors 24 from the respective anchor housings 30. Alternatively, each anchor 24 can be fully deployed one by one, omitting the partial deployment step. Once all anchors 24 desired are fully deployed to secure the implant into the annulus 4, the frame 20 can be withdrawn into the delivery catheter 16 and withdrawn with the delivery catheter 16 from the patient. In examples where a suture 56 or the like is utilized to secure the frame 20 to the implant 12, the suture 56 can be severed or otherwise disengaged from the frame 12 prior to withdrawal of the frame 20 from the patient.

Example 2

One method of the disclosure includes providing the system including an annuloplasty implant and a delivery device in a delivery arrangement. The delivery device includes, for example, a delivery catheter having a distal end and a sizing device at least partially housed within the delivery catheter. The sizing device has a frame including a plurality of struts and a plurality of anchor housings interconnected to at least one respective strut. One of a plurality of anchors is positioned within each of the anchor housings in a delivery arrangement. Then, the method can include directing the distal end to a mitral valve annulus of a patient and distally advancing the plurality of anchor housings out of the distal end. The plurality of anchor housings are then positioned around the mitral valve annulus. The plurality of anchors are advanced into the mitral valve annulus and are detached from the frame. The method can include withdrawing the frame into the delivery catheter and withdrawing the frame and the delivery catheter from the patient.

Optionally, each of the plurality of anchors are partially advanced into tissue prior to any one of the plurality of anchors being fully deployed into tissue; wherein, when partially deployed, the each anchor is connected to both the mitral valve annulus and the anchor housing. In one method, after the step of distally advancing the frame out of the distal end, an intra-cardiac echo catheter is delivered to the mitral valve annulus through the delivery catheter. In various methods, each anchor is threadably connected to one of the plurality of anchor housings in the delivery arrangement. In various methods, the annuloplasty implant includes a lumen and an elongated member extending through the lumen. In this example, the method can further include locking a position of the elongated member. Each of the plurality of anchors is selected from the group consisting of a helical anchor, a double helical anchor and a pronged anchor, for example. In various methods, the delivery device further includes a tube and the method further includes slidably engaging the tube with the frame to compress two adjacent struts. In various methods, the frame further includes a plurality of crowns and a manipulation wire secured to each crown. The method can also include moving at least one manipulation wire within an atrium to find the mitral valve annulus. Optionally, the annuloplasty implant is a fabric implant. In some methods of the disclosure, each of the plurality of anchors are rotatingly advanced into the mitral valve annulus. In one example, in the delivery arrangement, a position of the plurality of anchor housings are staggered with respect to a length of the delivery catheter.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

What is claimed is:

1. A system comprising:

an implant; and a delivery device including:

a delivery catheter, and a sizing device at least partially housed within the delivery catheter, the sizing device having a frame including a plurality of struts and a plurality of anchor housings interconnected to at least one respective strut; wherein one of a plurality of anchors is positioned within each of the anchor housings in a delivery arrangement;

wherein, in the delivery arrangement, the sizing device and the implant are positioned entirely within the delivery catheter and each anchor is within one of the plurality of anchor housings; the delivery device further having an adjustment arrangement in which the implant, anchors and at least a portion of the sizing device are positioned outside of the delivery catheter; the delivery device further having a deployed arrangement in which the frame is disconnected from the plurality of anchors and the frame is withdrawn into the delivery catheter.

2. The system of claim 1, further comprising one shaft connected to each anchor configured to selectively advance the respective anchor out of the respective anchor housing.

3. The system of claim 1, wherein, in the delivery arrangement, a position of the plurality of anchor housings are staggered with respect to a length of the delivery catheter.

4. The system of claim 1, wherein the struts are made of a shape memory metal.

5. The system of claim 1, further comprising a tube slidably engageable with the frame to compress two adjacent struts.

6. The system of claim 5, wherein the tube is engaged with the frame with threads.

7. The system of claim 5, wherein the frame includes a plurality of crowns interconnecting adjacent struts and the tube is engageable with one of the plurality of crowns.

8. The system of claim 1, wherein the implant includes a lumen and an elongated member extending through the lumen.

9. The system of claim 1, wherein each anchor of the plurality of anchors is selected from the group consisting of a helical anchor, a double helical anchor and a pronged anchor.

10. A method comprising:

providing a system including an implant and a delivery device in a delivery arrangement, the delivery device including:

a delivery catheter having a distal end, and a sizing device at least partially housed within the delivery catheter, the sizing device having a frame including a plurality of struts and a plurality of anchor housings interconnected to at least one respective strut; wherein one of a plurality of anchors is positioned within each of the anchor housings in a delivery arrangement;

directing the distal end to an annulus of a patient;

distally advancing the plurality of anchor housings out of the distal end;

positioning the plurality of anchor housings around the annulus;

advancing the plurality of anchors into the annulus;

detaching the plurality of anchors from the frame;

withdrawing the frame into the delivery catheter; and withdrawing the frame and the delivery catheter from the patient.

11. The method of claim 10, wherein each of the plurality of anchors are partially advanced into tissue prior to any one of the plurality of anchors being fully deployed into tissue; wherein, when partially deployed, the each anchor is connected to both the annulus and the respective anchor housing.

12. The method of claim 10, wherein after the step of distally advancing the frame out of the distal end, an intra-cardiac echo catheter is delivered to the annulus through the delivery catheter.

13. The method of claim 10, wherein each anchor is connected with threads to one of the plurality of anchor housings in the delivery arrangement.

14. The method of claim 10, wherein the implant includes a lumen and an elongated member extending through the lumen; the method further including locking a position of the elongated member.

15. The method of claim 10, wherein each of the plurality of anchors is selected from the group consisting of a helical anchor, a double helical anchor and a pronged anchor.

16. The method of claim 10, wherein the delivery device further includes a tube and the method further includes slidably engaging the tube with the frame to compress two adjacent struts.

17. The method of claim 16, wherein frame further includes a plurality of crowns and a manipulation wire secured to each crown; the method further including moving at least one manipulation wire within an atrium to find the annulus.

18. The method of claim 10, wherein the implant includes a fabric implant.

19. The method of claim 10, wherein each of the plurality of anchors are advanced using rotation, into the annulus.

20. The method of claim 10, wherein, in the delivery arrangement, a position of the plurality of anchor housings are staggered with respect to a length of the delivery catheter.

* * * * *